US010408735B2

(12) United States Patent
Hayden et al.

(10) Patent No.: US 10,408,735 B2
(45) Date of Patent: Sep. 10, 2019

(54) IN VITRO METHOD FOR THE LABEL-FREE DETERMINATION OF A CELL TYPE OF A CELL

(71) Applicant: Siemens Healthcare GmbH, Erlangen (DE)

(72) Inventors: Oliver Hayden, Herzogenaurach (DE); Oliver Schmidt, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 24 days.

(21) Appl. No.: 15/024,413

(22) PCT Filed: Sep. 30, 2014

(86) PCT No.: PCT/EP2014/070951
§ 371 (c)(1),
(2) Date: Mar. 24, 2016

(87) PCT Pub. No.: WO2015/052046
PCT Pub. Date: Apr. 16, 2015

(65) Prior Publication Data
US 2016/0231225 A1   Aug. 11, 2016

(30) Foreign Application Priority Data

Oct. 9, 2013   (DE) .......................... 10 2013 220 344
Jan. 20, 2014  (DE) .......................... 10 2014 200 911

(51) Int. Cl.
*G01N 15/14* (2006.01)
*G01N 15/10* (2006.01)
*G01B 11/06* (2006.01)
*G01N 15/00* (2006.01)

(52) U.S. Cl.
CPC ..... *G01N 15/1475* (2013.01); *G01B 11/0608* (2013.01); *G01N 15/10* (2013.01); *G01N 2015/008* (2013.01); *G01N 2015/0065* (2013.01); *G01N 2015/0073* (2013.01); *G01N 2015/1454* (2013.01); *G01N 2015/1493* (2013.01)

(58) Field of Classification Search
None
See application file for complete search history.

(56) References Cited

U.S. PATENT DOCUMENTS

| 7,812,959 B1 | 10/2010 | Kim |
| 8,406,498 B2 | 3/2013 | Ortyn et al. |
| 2006/0291712 A1 | 12/2006 | Popescu et al. |
| 2008/0032325 A1 | 2/2008 | Dimarzio |
| 2010/0060897 A1 | 3/2010 | Gustafsson |
| 2012/0021453 A1* | 1/2012 | Patra ............... G01N 15/147 435/34 |
| 2012/0034647 A1* | 2/2012 | Herzog ............. G01N 15/1475 435/34 |
| 2012/0114219 A1 | 5/2012 | Nakagawa et al. |
| 2012/0307035 A1 | 12/2012 | Yaqoob et al. |
| 2013/0171685 A1 | 7/2013 | Schutze et al. |
| 2013/0337496 A1* | 12/2013 | Hayden .................. C12Q 1/02 435/34 |
| 2014/0361148 A1 | 12/2014 | Popescu et al. |

FOREIGN PATENT DOCUMENTS

| CN | 101147052 A | 3/2008 |
| CN | 101149327 A | 3/2008 |
| CN | 101151518 A | 3/2008 |
| CN | 101346673 A | 1/2009 |
| CN | 102471744 A | 5/2012 |
| CN | 103328921 A | 9/2013 |
| DE | 102010023099 B3 | 11/2011 |
| WO | WO-2006/083917 A2 | 8/2006 |
| WO | WO 2007014622 A1 | 2/2007 |
| WO | WO 2009154558 A1 | 12/2009 |
| WO | WO 2010151221 A1 | 12/2010 |
| WO | WO 2013011000 A1 | 1/2013 |
| WO | WO 2013011001 A1 | 1/2013 |
| WO | WO 2013076089 A2 | 5/2013 |

OTHER PUBLICATIONS

International Search Report PCT/ISA/210 for International Application No. PCT/EP2014/070951 dated Jan. 5, 2015.
Written Opinion of the International Searching Authority PCT/ISA/237 for International Application No. PCT/EP2014/070951 dated Jan. 5, 2015.
Kemper. Björn et al: "Digital holographic microscopy for live cell applications and technical inspection"; Applied Optics. Optical Society of America; vol. 47; No. 4, pp. A52-A61; XP00790421 8 ; ISSN:0003-6935; DOI: 10.1364/AO.47.000A52; 2008.
Shaked, Natan T.: "Quantitative phase microscopy of biological samples using a portable interferometer", in: Optics Letters, vol. 37, No. 11, Jun. 1, 2012, pp. 2016-2018.

(Continued)

Primary Examiner — Emily A Cordas
(74) Attorney, Agent, or Firm — Harness, Dickey & Pierce P.L.C

(57) ABSTRACT

An in vitro method for the marker-free determination of a cell type of a cell in a biological sample is disclosed, a microscopic device being configured to detect a height profile of the cell with respect to a carrier plate. An embodiment of the method performed by a cell analysis device, include: determining a cell compartment of the cell on the basis of the detected height profile, determining a predetermined quantitative cell feature on the basis of the determined cell compartment, and determining the cell type of the cell on the basis of the determined quantitative cell feature. A correspondingly designed cell analysis device and a corresponding microscopic device are also disclosed.

13 Claims, 5 Drawing Sheets

(56) References Cited

OTHER PUBLICATIONS

Rommel, Christina et al: "Microinjection based 3-dimensional imaging of subcellular structures with digital holographic microscopy". XP009141890; DOI:10.1117/12.831582; 2009.
Kühn, Jonas et al: "Submicrometer tomography of cells by multiple-wavelength digital holographic microscopy in reflection", XP-001522472; vol. 34, No. 5; Optics Letters; 2009.
German Office Action dated Feb. 19, 2014.

\* cited by examiner

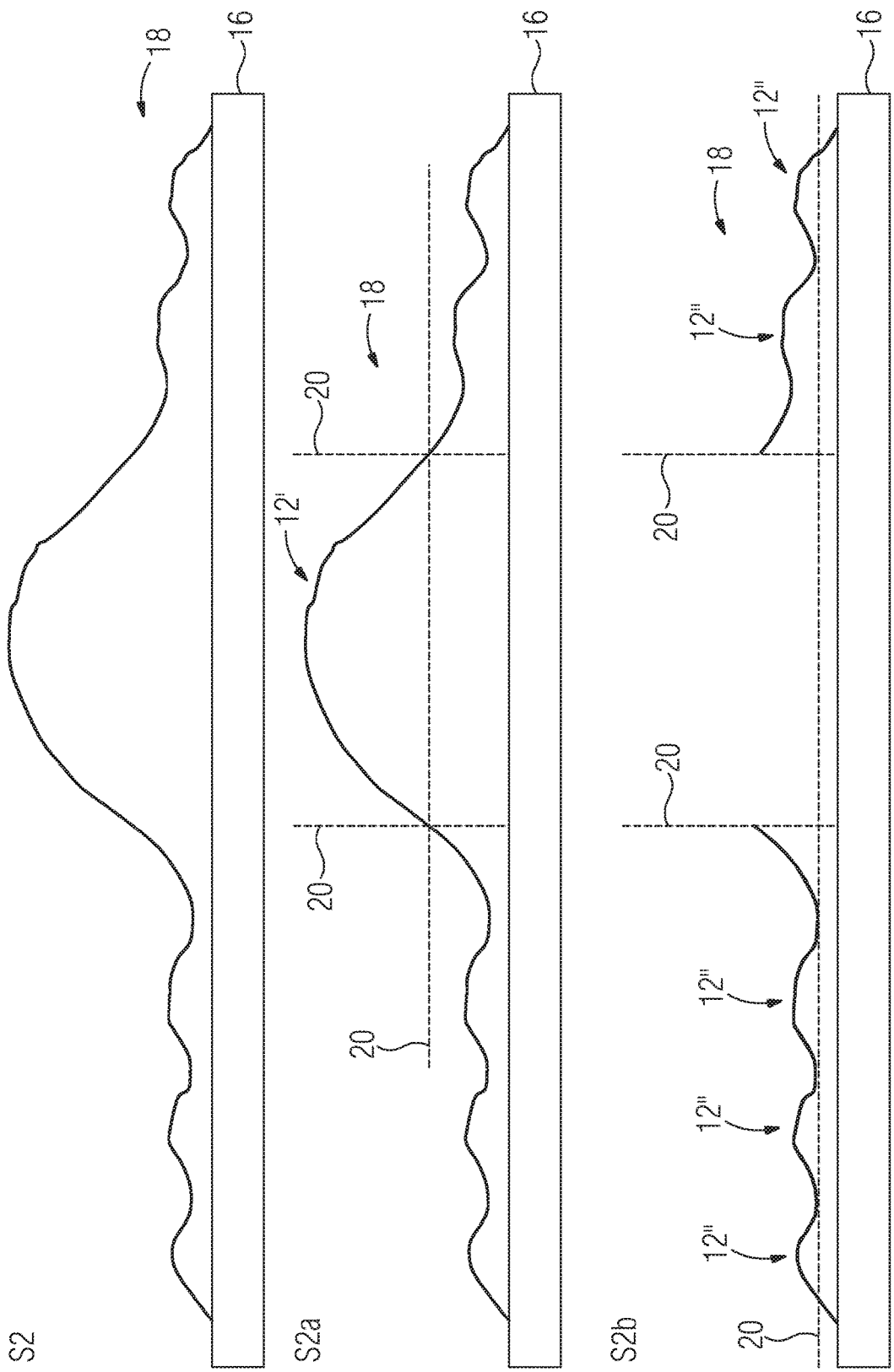

IN VITRO METHOD FOR THE LABEL-FREE DETERMINATION OF A CELL TYPE OF A CELL

PRIORITY STATEMENT

This application is the national phase under 35 U.S.C. § 371 of PCT International Application No. PCT/EP2014/070951 which has an International filing date of Sep. 30, 2014, which designated the United States of America and which claims priority to German patent application numbers DE 102013220344.6 filed Oct. 9, 2013 and DE 102014200911.1 filed Jan. 20, 2014, the entire contents of which are hereby incorporated herein by reference.

FIELD

An embodiment of the invention generally relates to a method for the marker-free determination of a cell type of a cell using a microscopy device.

BACKGROUND

Determining cells and allocating them to a cell type is very important in cytology. Cellular blood components, i.e. erythrocytes, thrombocytes and white blood cells, are determined and quantified in, for example, a hematological examination. Determination of the number of leucocytes (white blood count, WBC) should be able to differentiate the essential populations of the white blood cells for a comprehensive diagnosis. The white cells are differentiated according to granular cells (neutrophils, eosinophils, basophils) and non-granular cells (lymphocytes, monocytes). In addition to the granularity the cells also differ in respect of the fragmentation of the cell nucleus (without fragmentation: mononuclear cells, i.e. lymphocytes and monocytes; polymorphonuclear cells: eosinophils, basophils and neutrophils) and the cell size. A dye is used for the differentiation of the granular cells, in particular eosinophilic and basophilic granulocytes. The cell populations are conventionally evaluated by fully automatic hematology analyzers or by microscopy. Fully automatic analyzers have to analyze the populations according to fixed algorithms (with the aid of, for example, impedance, scattered light and absorption measurements). However, this often leads to error messages being displayed in the case of pathological samples, for example. In the next step microscopy conventionally takes place as a validation method for cells incorrectly determined by the hematology analyzer. This step is laborious and cost-intensive since it also requires manual evaluation in addition to sample preparation, microscopy and further work carried out manually.

It can also be important to determine the cell volume in addition to the morphology of the cell. Due to scattering by granules and polymorphic nuclei this is conventionally undertaken only in non-granular erythrocytes and platelets. Therefore, as a rule, this is not carried out for white blood cells.

In order, for example, to carry out quantitative blood cell diagnostics, a hematology analyzer can be dispensed with and instead each single cell can be examined using microscopy. This allows the blood count to be determined independently of fixed evaluation algorithms and flags. The drawback of this approach, however, is the lower sample throughput than with a hematology analyzer and the continued effort of immobilizing and dyeing the cells on microscope slides. These dyes also have only limited reproducibility, moreover, and exhibit a high dependency on humidity, dye life, temperature and more. A drawback of pure microscopy is quantifying the cell volumes compared to flow cytometers used in hematology analyzers.

An imaging flow cytometer is known from U.S. Pat. No. 8,406,498 whereby the differentiation of white blood cells can be determined directly. A dye is used in this case as well, however, to differentiate eosinophilic and basophilic granulocytes. The drawbacks mentioned above result here as well therefore.

SUMMARY

At least one embodiment of the invention provides a more efficient and more robust method for differentiating cells.

At least one embodiment of the invention is directed to a method; at least one embodiment of the invention is directed to a cell analysis device; and at least one embodiment of the invention is directed to a microscopy device. Advantageous developments of the invention are given by the claims.

At least one embodiment of the invention is directed to an inventive in vitro method for the marker-free determination of a cell type of a cell in a biological sample is carried out with the aid of a microscopy device and a cell analysis device. A microscopy device is a device with which very small objects can be viewed greatly enlarged and comprises, for example, a light microscope, a scanning electron microscope, a phase contrast microscope, a digital holographic microscope or a microscope having an ultrasound sensor (for example an acoustic microscope). The microscopy device detects a height profile of the cell with respect to a carrier plate. A height profile is a profile which describes the position and height of the cell, i.e. provides topographical information.

A cell analysis device, i.e. a device or a device component, which is suitable for electronic data processing and is designed to process data of a height profile, carries out at least:

determining a cell compartment of the cell using the detected height profile,
determining a predetermined quantitative cell feature using the determined cell compartment, and
determining the cell type of the cell using the determined quantitative cell feature.

At least one embodiment is also directed to a cell analysis device, for example a microchip or a microcontroller, which is set up to carry out one or more of the above-described embodiment(s) of the method.

At least one embodiment is also directed to a microscopy device for marker-free determination of a cell type of a cell of a biological sample, comprising an embodiment of the above-mentioned cell analysis device. The microscopy device preferably comprises a digital holographic microscope.

BRIEF DESCRIPTION OF THE DRAWINGS

The invention will be illustrated again in more detail with reference to the accompanying drawings by specific example embodiments. The illustrated examples are preferred example embodiments. Elements with the same function have the same reference numerals in the FIGURES, in which:

FIG. 3 shows a schematic view of the determination of a cell compartment and the determination of a predetermined quantitative cell feature according to one embodiment of the inventive method.

DETAILED DESCRIPTION OF THE EXAMPLE EMBODIMENTS

Figure 1:
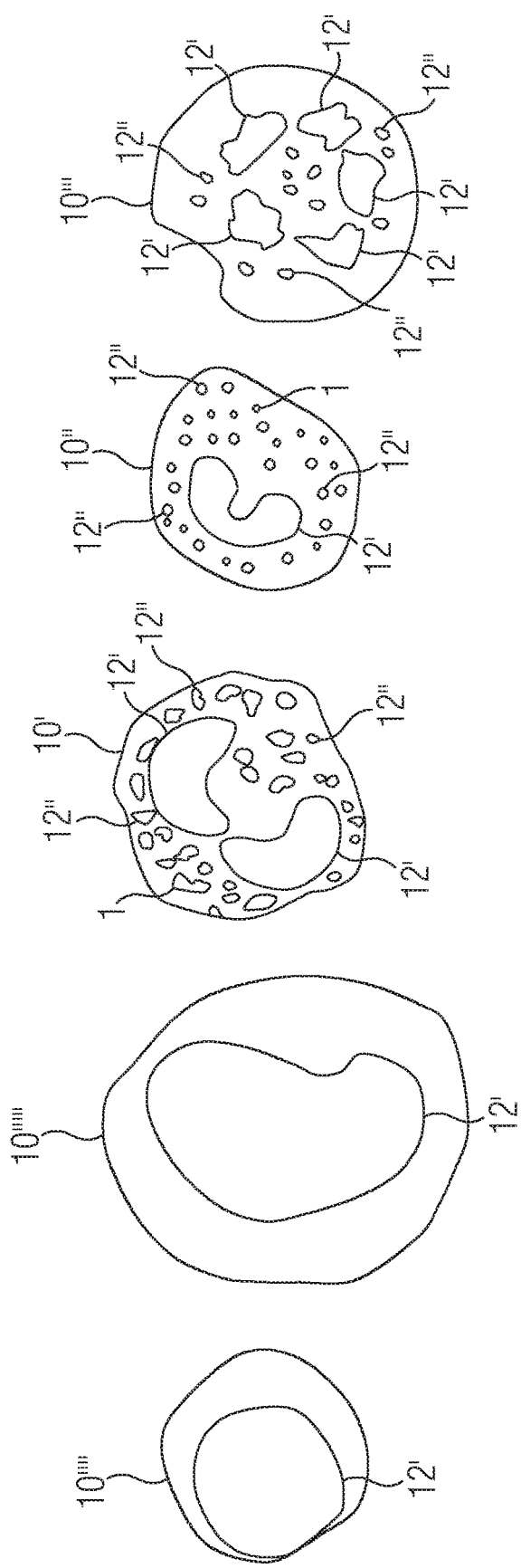
FIG. 1 shows a sketch relating to the five fundamental cell types of a white blood cell population.

At least one embodiment of the invention is directed to an inventive in vitro method for the marker-free determination of a cell type of a cell in a biological sample is carried out with the aid of a microscopy device and a cell analysis device. A microscopy device is a device with which very small objects can be viewed greatly enlarged and comprises, for example, a light microscope, a scanning electron microscope, a phase contrast microscope, a digital holographic microscope or a microscope having an ultrasound sensor (for example an acoustic microscope). The microscopy device detects a height profile of the cell with respect to a carrier plate. A height profile is a profile which describes the position and height of the cell, i.e. provides topographical information.

A cell analysis device, i.e. a device or a device component, which is suitable for electronic data processing and is designed to process data of a height profile, carries out at least:
  determining a cell compartment of the cell using the detected height profile,
  determining a predetermined quantitative cell feature using the determined cell compartment, and
  determining the cell type of the cell using the determined quantitative cell feature.

Within the context of at least one embodiment of the present invention a cell compartment is taken to mean the cell region which is surrounded by a biomembrane. A cell compartment will consequently hereinafter be taken to mean, for example, a mitochondrion, a cell nucleus, a vacuole, the cytoplasm or a granule, wherein a granule, i.e. a visible, grain-shaped deposit of the cell, is taken to mean a cell compartment, and a plurality of granules is taken to mean a plurality of cell compartments.

At least one embodiment of the inventive method provides a robust and marker-free method for determining a cell type. At least one embodiment of the inventive method is equally suited to determining a cell type of a cell and to determining cells of a heterogeneous cell suspension. The ability to dispense with dyeing processes of cells means the determination of cells is not affected by physical properties of the dye.

Unlike in conventional pre-analysis, the use of rounding buffers (for example a diluted SDS buffer solution) can be dispensed with when carrying out the inventive method. This almost completely prevents rounding of cells and the occurrence of artifacts. Forming of echinocytes from erythrocytes, for example, can therefore be prevented during blood analysis.

Because the dyeing process has been dispensed with the method also allows a high sample throughput and allows a qualitative and/or quantitative determination of cells independently of fixed evaluation algorithms or binary status indicators. Microscopy with a high sample throughput is consequently enabled and conventional hematology analyzers can be dispensed with.

If, according to a further embodiment of the inventive method, the predetermined quantitative cell feature is determined using the height profile, then this leads to a higher resolution and therewith to a more accurate determination of the cell type. Alternatively, an additional quantitative cell feature can be used which is not determined using the height profile but, for example, to determine the cell type using an intensity, polarization or fluorescence.

A further, particularly preferred improvement to determination of the cell characteristics can be achieved in that the cell compartment is ascertained by determining a cell volume, determining a first cell compartment, for example the cell nucleus, and determining a further cell compartment. Determining a cell compartment can comprise, for example, segmenting the cell compartment. This constitutes a particularly preferred embodiment of the inventive method. The region of the first compartment can be ignored, for example, when determining the second compartment.

In a further embodiment of the inventive method the quantitative cell feature can describe, for example, a cell volume, a volume of the cell compartment, a cell area, an area of the cell compartment, a ratio of a cell volume to a cell nucleus volume, a ratio of a cell area to a cell nucleus area, a diameter of the cell compartment, a roundness of the cell compartment, a circumference of the cell compartment, a number of the cell compartment and/or a statistical feature of a cell feature which is determined using the respective height profile of a plurality of cells and/or using the height profiles of a plurality of cell compartments. This enables a large number of indirect characteristics which increase the application possibilities of the inventive method.

In a particularly preferred embodiment of the inventive method the quantitative cell features describes a statistical feature of a cell feature which is determined using the respective height profiles of a plurality of cells and/or using the height profiles of a plurality of cell compartments. This enables a higher resolution in the classification of the cells and improved distinguishability, in particular between different cells which are difficult to differentiate on the basis of conventional methods. The statistical feature is preferably a variance of the diameter of the same cell compartments, for example a variance of the diameter of the granules and/or a mean diameter of the cell compartments, in particular a mean diameter of the granules as a cell compartment.

Furthermore, a statistical feature based on a plurality of cells can be used. For example, the mean diameter of the cell nucleus of a large number of, for example, white blood cells as cells can be related to the diameter of the cell nucleus of the cell being examined.

The height profile is preferably used to detect the cell features, although additional information can be detected in further embodiments, and this can be additionally provided as a function of the microscopy method. For example, the intensity distribution, a polarization or fluorescence contrast can also be used to enable better differentiation.

Particularly good results in the differentiation of a heterogeneous cell mixture, which comprises a plurality of different cell types which are difficult to differentiate, are achieved according to a further embodiment of the inventive method in which the cell type is determined using a combination of the determined quantitative cell feature with a further determined quantitative cell feature.

The cell type of the cell is preferably determined in a first classification step of the cell using the combination of the number of cell compartments and the ratio of the cell area and the area of the cell compartment and in a further classification step using the combination of a variance in the diameter of the cell compartment and a mean diameter of the cell compartment. This embodiment of the inventive method proves itself in particular with complicated cell suspensions analyses, for example with a differential blood count, in which, for example, white blood cells are differentiated.

The height profile is preferably detected by superimposing a reference wave on an object wave, recording a resulting interferogram and/or a mathematical reconstruction, for example by means of phase contrast microscopy. This particularly advantageous embodiment of the inventive method is particularly suitable for determining quantitative features; it primarily favors marker-free differential blood analysis. The images obtained by phase contrast microscopy can be particularly well reproduced and have a high resolution.

The use of digital holographic microscopy is particularly advantageous since it allows the phase information of the object to be acquired quantitatively. According to a further embodiment of the inventive method the height profile is therefore determined by means of digital holographic microscopy, interference phase microscopy or quantitative phase microscopy. These microscopy methods allow particularly high axial resolution, i.e. in the direction of the optical axis of the microscope. Digital holographic microscopy allows a resolution of up to 1 nm in the z direction. This corresponds to a precision which is higher by a factor of 100-1,000 than with other known light microscopic methods (for example confocal microscope). More accurate determination of the cell type is possible therefore owing to the precise determination of the height profile.

A further advantage is achieved if the method is carried out with one or more undyed and/or undried cell(s). Since the vitality of the cells is not affected by the inventive method, the cells determined by the method can continue to be used for impact analyses after the determining method is concluded.

According to a further example embodiment the inventive method can comprise phenotyping of the cell with a marker and/or expressing a predetermined receptor for further allocation of the cell. This enables extensive molecular biological examination of the determined cell.

At least one embodiment of the inventive method obtains particular relevance if it is carried out according to a further embodiment using a whole blood sample and/or the biological sample comprises blood cells, leucocytes, eosinophilic and/or basophilic leucocytes. This is primarily used when determining a blood count in hematology.

In a further embodiment the cell type can be determined to differentiate neutrophils, eosinophils, basophils, lymphocytes and/or monocytes, and/or comprises determining cell functionality, in particular determining an activation state of a cell, for example a thrombocyte, and/or detection of a cell, for example a deformed erythrocyte and/or a pathogen-affected cell.

According to a further embodiment of the inventive method, determination of the cell type can comprise determination of a cell stage of the cell, in particular for differentiating a cell age, a physiological or morphological state of the cell or an activity state of the cell. This allows an image sequence of, for example, activation processes of a cell to be recorded.

At least one embodiment is also directed to a cell analysis device, for example a microchip or a microcontroller, which is set up to carry out one or more of the above-described embodiment(s) of the method.

At least one embodiment is also directed to a microscopy device for marker-free determination of a cell type of a cell of a biological sample, comprising an embodiment of the above-mentioned cell analysis device. The microscopy device preferably comprises a digital holographic microscope.

With the aid of an embodiment of the inventive in vitro method a cell type of a cell in a biological sample can be determined in a marker-free manner. Here marker-free means that the cells do not have to be marked by, for example, fluorescence dyes or radioactive particles. A biological sample can, for example, comprise a sample of animal or plant cells, bacterial cells and/or protozoa. It is preferably a whole blood sample which comprises, for example blood cells $10$, for example leucocytes, eosinophilic granulocytes or basophilic granulocytes. For reasons of clarity the different example cell types are identified in FIG. 1 and in FIGS. 2, 3, 4a and 4b with the following reference numerals: eosinophilic granulocytes $10'$, basophilic granulocytes $10''$, neutrophilic granulocytes $10z'''$, lymphocytes $10''''$ and monocytes $10'''''$. For reasons of legibility the reference numeral $10$ is used, however, for each cell type in the following description of the example embodiments.

In the example of FIG. 1, for example, five fundamental white blood cells are shown which are differentiated in the case of a small blood count. The white blood cells comprise granular cells $10$, for example eosinophilic granulocytes $10$, basophilic granulocytes $10$ and neutrophilic granulocytes $10$. The non-granular cells $10$ include lymphocytes $10$ and monocytes $10$. FIG. 1 shows, for example, one cell $10$ of each cell type. The example non-granular cells $10$ each have a cell nucleus $12$. The remaining example granulocytes $10$ have irregularly lobed cell nuclei $12$, in other words are polymorphonuclear. Common to all the granular cells $10$ is that they have, for example, a plurality of granules $12''$ in their interior. For the sake of clarity only some of the granules $12''$ in these cells are identified with reference numerals in FIG. 1. The white blood cells $19$ also differ in their cell size.

The cell nucleus $12'$ and the granules $12''$ are mentioned merely by way of example as cell compartments $12$ in this example embodiment. Alternative cell compartments $12$ are, for example, a mitochondrion, a vacuole, a cytoplasm or an endoplasmatic reticulum.

Figure 2:
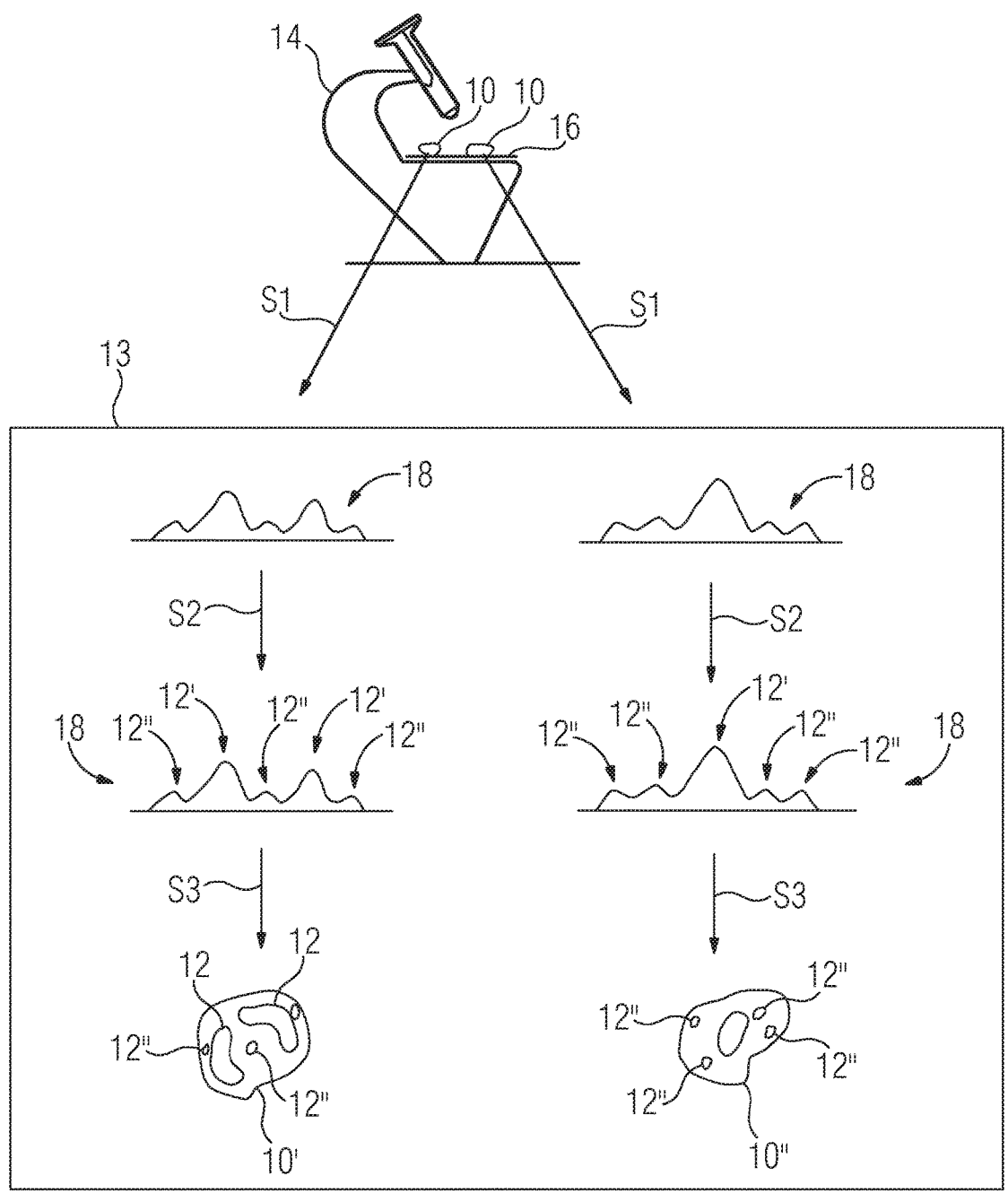
FIG. 2 shows a schematic sketch relating to an embodiment of the inventive method.

FIG. 2 schematically shows the principle of an example embodiment of the inventive method. FIG. 2 shows a microscopy device $14$ which is designed to precisely determine topography, i.e. height information of a cell. The resolution of the height information is at least 1 micrometer, preferably 100 nanometers or less than 100 nanometers, particularly preferably 10 nanometers or less than nanometers. As in the example of FIG. 2, the microscopy device $14$ preferably comprises a digital holographic microscope.

Digital holographic microscopy (DHM), also called interference phase microscopy, is characterized in that it can quantitatively detect the intensity as well as the phase of an object in a scan. An intensity distribution, which is produced due to absorption and scattering of light on the object, is not recorded for this purpose, as is conventional in microscopy. Instead, a wave front, which results from the superimposition of an object wave and a reference wave, is recorded. The intensity and phase information of the object can be reconstructed therefrom with the aid of a computer.

This microscopy method is suitable for examining biological samples since these are substantially transparent for visible light without further sample preparation and therefore have a low contrast in a conventional microscope. Recording the phase information makes it possible to detect the morphology of the cell very precisely and to undertake a differentiation of the cell with the aid of this information.

Compared to conventional phase contrast microscopes, which are conventionally implemented by a phase annulus in the objective and an annular orifice in the condenser, DHM has the advantage that the phase can be quantitatively determined. Accordingly quantitative phase contrast microscopy is also referred to. It is only the quantification of the phase that enables a reproducible reconstruction of the height profile of the object, and only thereby can the cell type be automatically determined.

Reference should be made to the fact that the phase shift of the light is determined by the optical path length through the object, i.e. the geometric thickness of the object as well as the refractive index play a part in this connection. To obtain a real geometric height profile from the phase information, the refractive index of the sample must be known. In a preferred application of microscopy of cells a largely constant and known refractive index can be assumed, however, whereby the phase information can be directly converted into a height profile. Alternatively, the phase information can be recorded at different wavelengths and the effect of the refractive index be calculated therefore as a result.

It should also be noted that the phase information is uniquely determined only at one phase angle of 360°. A measured phase shift of, for example, 10° can correspond in reality to a phase shift of 370°, 730°, etc. The uniqueness range is accordingly limited to the wavelength of the light. In the chosen application this limitation can likewise be ignored in the microscopic examination of cells since biological cells do not have steep sides and therefore the phase vales of the adjacent pixels are provided as a connecting condition.

With the aid of the microscopy device 14 a height profile 18 of a respective cell 10 is detected (method step S1), and this is determined, for example, from a digital hologram, height profile or an interferogram. If the microscopy device 14 comprises, for example, an acoustic microscope, the height profile can be determined from a sonogram. Method step S1 comprises, for example, recording a hologram, an iterative reconstruction of the phase and/or intensity information of the object and/or a conversion of the phase information into a height profile.

Two cells 10 on a carrier plate 16 are shown here by way of example. Detecting the height profile 18 comprises detecting a cell contour, i.e. a height profile of the cell surface in relation to the carrier plate 16. The carrier plate 16 can comprise, for example, a slide or another substrate for microscopic examinations familiar to a person skilled in the art. A continuous strip, made, for example, of a polymer, can also be used for high-throughput microscopy, and this is continuously pulled under the objective. FIG. 2 also shows a cell analysis device 13 which carries out method steps S2 and S3.

In the example embodiment described here the example cells 10 are determined, for example white blood cells are differentiated, and this is based, for example, on reconstructed phase information of the cells 10. For this purpose firstly one or more cell compartment(s) 12 of the cell 10 is/are determined using the detected height profile 18 (S2). In the example of FIG. 2 the left-hand height profile 18 of the first example cell 10 shows two pronounced elevations which point, for example, to the presence of a polymorphous cell nucleus 12'. In addition, for example, three smaller elevations of the height profile 18 can be seen, and these point toward three granules 12". Compared with this, the height profile 18 of the second cell 10 points toward a mononuclear cell nucleus 12' and four granules 12". A predetermined quantitative cell feature is determined in further method step S3, for example a number of one of the cell compartments 12 or a diameter of one of the cell compartments 12, using the determined cell compartment 12. The cell type of the cell 10 is then determined using the qualitative cell feature (S3). In the example of FIG. 2 an eosinophilic granulocyte 10 (on the left in the picture) and a basophilic granulocyte 10 (on the right in the picture), for example, are determined using the height profile 18.

FIG. 3 shows a schematic view of the determination of the cell compartment 12 (S2). The very top of the picture shows an example height profile 18 of a cell 10 on a carrier plate 16 for this purpose. In a first step, for example, a cell volume of the cell 10 is determined for this purpose. Methods for determining the cell volume using a height profile are known to a person skilled in the art from the prior art (e.g. integration or summation of the height over the entire area of the cell). The area of the cell can take place, for example, on the basis of a threshold value in absorption contrast or in the height profile.

In a further intermediate step S2a (see middle illustration of FIG. 3) subsequent segmenting of one of the cell compartments 12, in the present example of the cell nucleus 12' as the first cell compartment 12, is indicated. Segmenting takes place on the basis of the height information for this cell compartment 12. Segmenting can take place, for example, by way of the provision of an interferogram by a phase contrast method. When an alternative microscopy device 14 is used, provision of the height profile can include, for example, lasing, screening or ultrasound-linked scanning. The middle illustration of FIG. 3 shows two auxiliary lines 20, with the two vertical auxiliary lines 20 limiting the segment of the height profile 18 that describes the example first cell compartment 12' and with the horizontal auxiliary line 20 marking a predetermined threshold value which describes, for example, a value of 50 percent of the height of the first cell compartment 12'. For the remaining part of the cell 10 this threshold value is calculated, for example, from the mean height and, for example, the maximum height of the segmented region in order to thereby determine, for example, a diameter of the cell compartment 12 or the further cell compartment 12 and its number. A person skilled in the art can use several standard methods for segmenting the first cell compartment 12, such as, for example, determining a mean height with the aid of a matrix with image points and a height value. In addition, an angle that describes a tilted plane of the carrier plate 16 can be taken into account in the calculation.

In other words, different cell compartments 12, for example, can be segmented with different threshold values or selection criteria. The area of the first compartment is not considered further in order to determine a further cell compartment 12. If, for example, the first cell compartment 12 is the cell nucleus 12' and if the second cell compartment is a granule 12" or a plurality of granules 12", it can be assumed, for example in a second segmenting process, that there are no granules 12" at the site of the cell nucleus 12'.

Method step S2b (bottom of FIG. 3) shows the determination of the cell compartment 12. For this purpose a further contrast mechanism, for example, can be incorporated by determining a further base line 22. This further base line 22 can, for example, represent a further threshold value for a further cell compartment 12. In the present example a threshold value is chosen, for example, to determine one or more granule(s) as the cell compartment 12". A number, diameter and/or a mean size of granules, for example, can be determined hereby. Alternatively or additionally, a number of the cell compartment 12" per cell area, for example, can be determined.

Figure 4A:
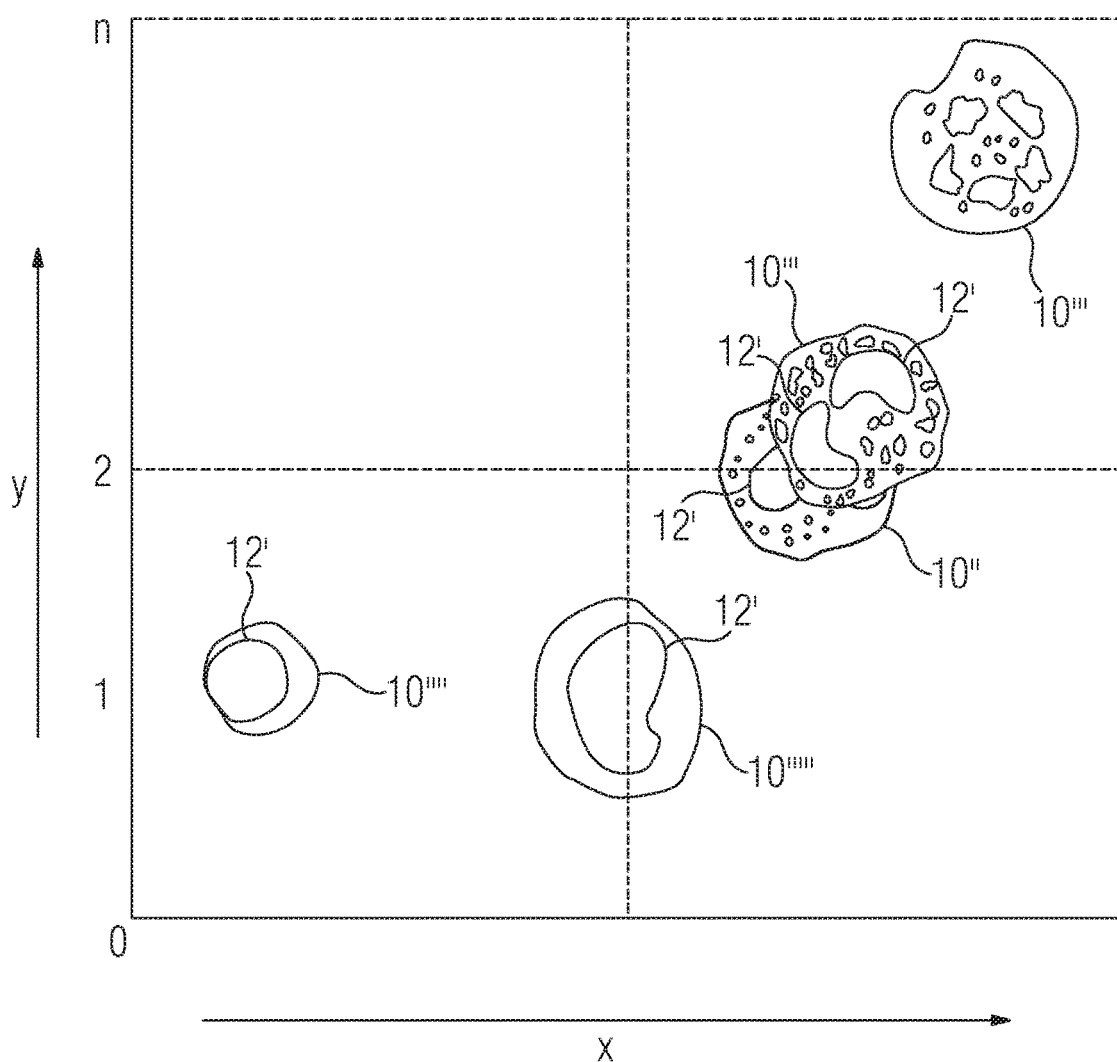
FIGS. 4a, 4b show a schematic sketch for determining the cell type of the cell with reference to determined quantitative cell features.
Figure 4B:
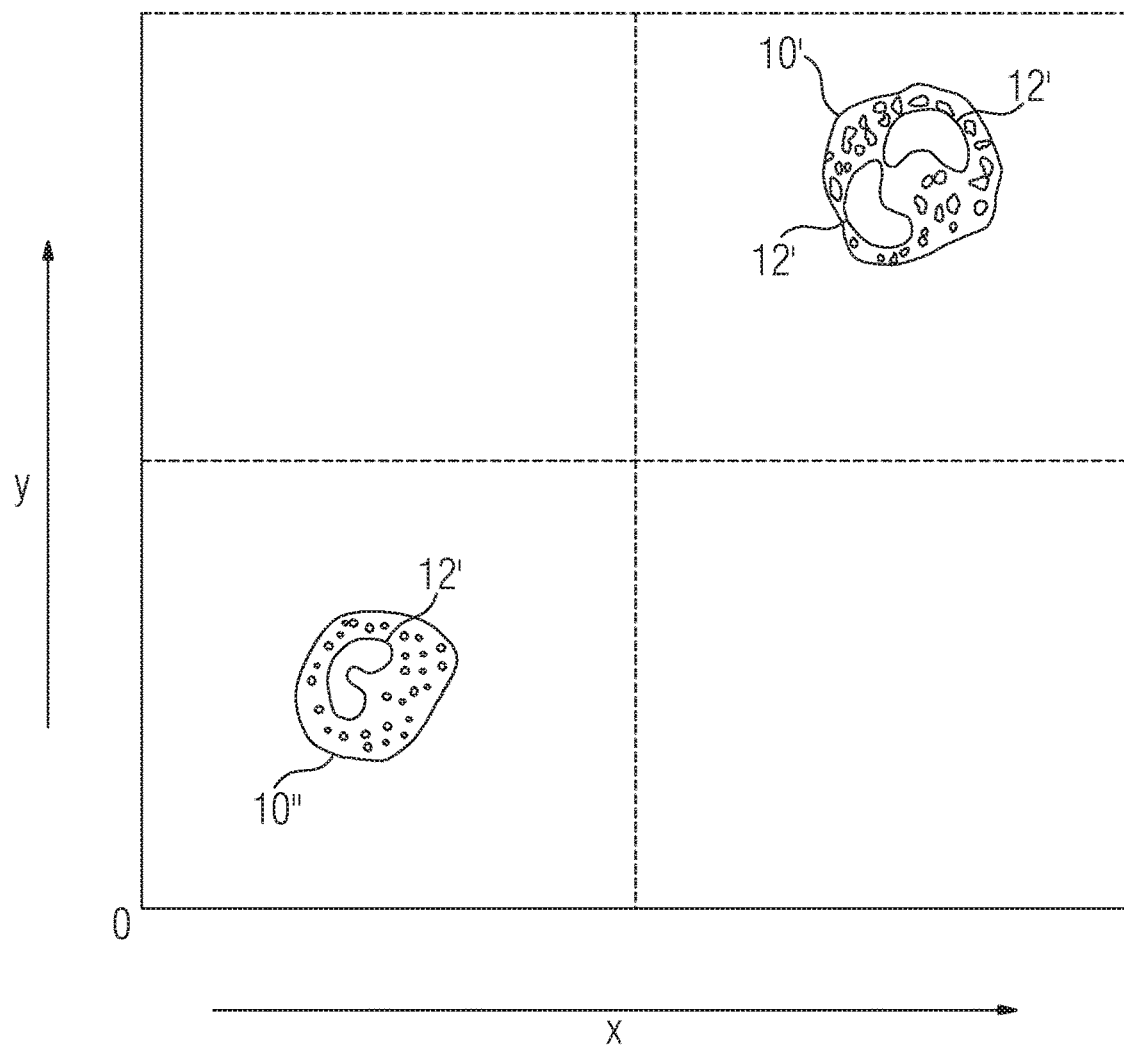

In the present example embodiment quantitative cell features are determined by way of example by a number of a cell nucleus, a ratio of a cell area to an area of the cell nucleus, a mean diameter of the granules and a variance in the diameter of the granules. Alternatively or additionally, for example a cell volume, a volume of the cell compartment, a cell area, an area of the cell compartment, a ratio of a cell volume to a cell nucleus volume, can be detected by means of quantitative cell features. FIG. 4*a* and FIG. 4*b* show the determination of the cell type of the cell 10 using the determined cell feature. FIG. 4*a* shows a matrix for classifying a cell 10 or a plurality of cells 10 whose ordinate Y denotes, for example, a number of the reference compartment 12, for example, a lobed quality of a cell nucleus 12' and whose abscissa X denotes, for example, a ratio of a cell area to an area of the cell nucleus. Additional broken auxiliary lines 20 are shown to illustrate the classification. If the cells 10 of the example cell mixture are classified in the matrix according to said example quantitative cell features then lymphocytes 10, monocytes 10 and neutrophilic granulocytes 10 that are present may be clearly determined. A further cluster is formed, for example, by basophilic granulocytes 10 and eosinophilic granulocytes 10.

Example granulocytes can be clearly differentiated from each other as early as in illustrated step S3*a*. Improvement in differentiating the example basophilic granulocytes 10 and eosinophilic granulocytes 10 may be achieved by further classification according to further quantitative cell features. This is shown in FIG. 4*b*. It has proven to be particularly advantageous in this connection if the example two further quantitative cell features describe a statistical feature of a cell feature which is determined using the respective height profiles of a plurality of cells 10. In the example of FIG. 4*b* a variance in a diameter of the granules, for example, is plotted on the ordinate Y whereas a mean diameter of the granules is plotted on the abscissa X. The matrix, which by way of broken lines is intended to facilitate classification here as well, clearly shows a separation of the cells 10.

The above-described example embodiment can take place, for example, in order to determine the cell functionality of the cell 10, in particular as a determination of the functionality, for example, of a white blood cell and/or a non-peripheral blood cell and/or a pathogen-affected cell 10. The functionality of a white blood cell can be determined, for example, using the change in volume, the change in the number of granules and/or the change in the cell nucleus. Examples of non-peripheral blood cells 10 are, for example, bone marrow cells and immature cells. The described method can also take place, for example, during the course of a lavage in the case, for example, of an infection or an examination of cerebrospinal fluid in the case of an infection. This also enables marker-free determination of a parasitic infection, such as, for example, determining malaria parasites in erythrocytes in defined cell cycle stages, wherein an early diagnosis is desired.

Alternatively or additionally, determination of the cell type can comprise a determination of a cell stage of the cell 10, in particular for differentiation of a cell age, for example of the age of granular neutrophilic granulocytes, wherein, for example, a shift occurs in the classification matrix in the case of, for example, young rod-shaped neutrophils compared to mature, round neutrophils. A physiological or a morphological state of a cell 10 can also be determined, for example within the context of detection of a pathological blood diagnosis by over-segmented nuclei of neutrophilic granulocytes due, for example, to an iron deficiency. A further example is the detection of, for example, deformed erythrocytes, for example echinocytes in the presence, for example, of sickle cell anemia. A further example is the determination of the cell type within the context of a size distribution of erythrocytes to differentiate reticulocytes, i.e. young erythrocytes. A differentiation of, for example, resting and/or activated thrombocytes by way of a change in the morphology can also be carried out within the context of the described inventive method.

A currently used approach for creating a differential blood count can be carried out marker-free by the inventive method. An example procedure for creating a differential blood count comprises, for example, determining a cell size, a maturation state of the cell, i.e. an age of the cell, a core plasma ratio, detection of cytoplasmic inclusions and detection of a chromatin structure.

The example embodiment mentioned above clarifies the inventive principle of detecting at least one cell compartment 12 of a cell 10 with the aid of a height profile 18 detected by a microscopy device and determining a quantitative cell feature using the determined cell compartment 12 and/or the height profile 18.

Ideally, an automatable and marker-free microscopy technique is used to minimize sample preparation steps, such as, for example, dyeing cells 10, and, moreover, to enable marker-free determination of a quantitative cell feature, for example a volume determination of the cell 10. Interference microscopy or digital holographic microscopy is preferably used, and this enables, for example, a marker-free differential blood count examination of, for example, white blood cells 10 since it can use, for example, the granularity, cell nucleus morphology and cell volumes to differentiate, for example, eosinophilic and basophilic granulocytes 10. This simultaneously constitutes the greatest challenge in the differentiation of, for example, white blood cell populations.

Different cell types can be differentiated on the basis of, for example, the morphology of the cell 10. While, for example, lymphocytes, monocytes and neutrophils can be differentiated very easily owing to, for example, their different size and cell nucleus morphology, an increased demand is placed on the differentiation of, for example, eosinophilic and basophilic granulocytes.

Topographical information by means of, for example, digital holographic microscopy (DHM) is used for differentiation. In a first step a cell compartment 12, for example a cell nucleus 12', is segmented on the basis of the height information. A threshold value (for example 50 percent) is then calculated for the remaining part of the cell 10 from, for example, the mean height and, for example, the maximum height of the segmented region in order to thereby determine, for example, a diameter of the granules and their number (FIG. 3). The differentiation can then be derived from this parameter (FIG. 4*a*, FIG. 4*b*). For example, a size and a form of a cell nucleus 12' can be used to differentiate, for example, lymphocytes, monocytes, neutrophilic, eosinophilic and basophilic granulocytes (FIG. 4*a*). The following quantitative cell features can be used by way of example for this: a ratio of volume of the cell 10 to volume of the cell nucleus 12', a number and/or volume of, for example, polymorphic cell nuclei 12', information about number, diameter and size distribution of, for example, the granules, which are then used to differentiate, for example, eosinophilic and basophilic granulocytes (see FIG. 4*b*).

Interference microscopy, also called digital holographic microscopy (DHM), is characterized in that it can quantitatively detect an intensity as well as a phase of an object in a scan. For this purpose a wave front, which results from the superimposition of an object wave and a reference wave, is detected instead of an image of the object, as is conventional in microscopy. Intensity information and phase information of the object can be reconstructed from this with the aid of a cell analysis device, for example a computer.

These microscopy methods are suitable for an examination of biological samples since they are substantially transparent for visible light without further sample preparation and therefore have a lower contrast in a conventional microscope. By recording the phase information it is possible to detect the morphology of the cell 10 very precisely and to undertake a differentiation of the cell 10 with the aid of this information.

A differentiation of, for example, white blood cells, based on, for example, reconstructed phase information of a plurality of cells 10 can be carried out without it being necessary to dye the cells 10, and it is consequently possible to work with fresh, undried cells. As a result, unnecessary artifacts, which are produced by different ways of handling the samples during drying and dyeing, are avoided. The images can be reproduced and can be differentiated more easily due to automatic computer-assisted image processing. The number of process steps is minimized. Costs and time are saved and reliable and fast diagnosis is made possible as a result.

During pre-analysis the use of, for example, rounding buffers (i.e. highly diluted SDS buffer solution) can therefore be dispensed with compared to hematology analyzers. A rounding buffer would lead to rounding of cells which while suitable for scattered light measurement with a flow cytometer simultaneously leads to artifacts. Erythrocytes, for example, are very sensitive and form echinocytes.

At least one embodiment of the invention comprises at least one of the following aspects:

1. A method for differentiating blood cells, based on:
a) recording an interferogram of the object,
b) reconstruction of the phase information of the object, and
c) processing the phase images to differentiate the different blood cells.

2. Apparatus for differentiating blood cells, comprising:
a) a digital holographic microscope.
b) reconstruction software for calculating the phase information of the object, and
c) automated image processing to differentiate the various blood cells.

Features for further independent aspects of embodiments comprise at least one of:
development of the interferogram by superimposing a reference wave on the object wave
using the phase information in order, for example, to determine the volume of a complete cell 10 or individual segments of the cell 10,
using undyed and undried blood cells,
the example blood cells to be differentiated are, for example, leucocytes,
the example leucocytes to be differentiated are, for example, eosinophils and basophils,
the ratio of cell volume to cell nucleus volume, for example, is used for differentiation,
a diameter of the cell compartment 12, for example, of a plurality of granules, for example, is used for differentiation,
a number of cell compartments, for example, of the granules, for example, is used for differentiation,
a differentiation is achieved, for example, in a multi-stage process, for example firstly on the basis of the cell nucleus volume and then, for example, on the basis of granule information,
a combination of, for example, interference microscopy and immunophenotyping with, for example, markers comprising, for example, antibodies and nanoparticles, for example a contrasting particle comprising, for example gold, magnesium or silica; additionally or alternatively an expression of, for example defined receptors for further differentiation of the cell type.

At least one embodiment of the invention comprises at least one of the following aspects that go beyond an example differentiation of, for example, eosinophilic and basophilic granulocytes:
microscopy of, for example, a plurality of cells 10, for example, directly in blood plasma, preferably close to in vitro conditions; for example citrated blood, heparinized blood, EDTA blood to prevent blood clotting,
an activation of the, for example, granular cells 10 without marking can be examined under a microscope (for example the change in, for example, granules 12" which are discharged, by way of example, by granulocytes 10),
a differentiation of, for example, an age of, for example, granular neutrophils can be achieved without marking ("shift left" corresponds to young, strong-nucleus neutrophils),
detection of a pathological blood diagnosis by, for example, over-segmented nuclei of neutrophils due, for example, to iron deficiency (diction: "right shift"),
detection of, for example, deformed erythrocytes (for example echinocytes, sickle cell anemia),
a size distribution of, for example, of erythrocytes for the differentiation of reticulocytes (young erythrocytes),
a differentiation of resting and activated thrombocytes due to a change in morphology,
microscopy of, for example non-peripheral blood cells (for example bone marrow; immature cells), lavage (infections) cerebrospinal fluid (infections),
marker-free determination of a parasitic infection (for example malaria, i.e. parasites in erythrocytes in defined cell cycle stages; early diagnosis desired).

A current procedure in a differential blood count can consequently be carried out marker-free using, for example, an interference microscope 14: for example cell size, maturity, nucleus-plasma ratio, cytoplasm inclusions, chromatin structure.

The invention claimed is:

1. An in vitro, marker-free method for distinguishing a leukocyte in a biological sample comprising cells, the method comprising:
detecting a height profile of a cell in the biological sample with respect to a carrier plate with a microscopy device;
identifying a cell compartment of the cell using the detected height profile;
determining a quantitative cell feature using the identified cell compartment; and
distinguishing the cell by comparing the quantitative cell feature of the cell to an equivalent quantitative cell feature of a known leukocyte; and determining whether the quantitative cell feature of the cell is similar to the equivalent quantitative cell feature of the known leukocyte, thereby distinguishing the type of leukocyte of the cell.

2. The method of claim 1, wherein the quantitative cell feature corresponds to at least one of a cell volume, a volume of the cell compartment, a cell area, an area of the cell compartment, a ratio of a cell volume to a cell nucleus volume, a ratio of a cell area to a cell nucleus area, a diameter, a roundness or a circumference of the cell compartment, a number of cell compartments of the cell and a statistical feature of a cell feature which is determined using the respective height profile of a plurality of cells.

3. The method of claim 1, comprising distinguishing the cell by comparing two quantitative cell features of the cell to two equivalent quantitative cell features of the known leukocyte.

4. The method of claim 1, wherein the height profile is determined by at least one of superimposing a reference wave on an object wave, recording a resulting interferogram and a mathematical reconstruction.

5. The method of claim 1, wherein the height profile is detected via digital holographic microscopy, interference phase microscopy or quantitative phase microscopy.

6. The method of claim 1, wherein the method is carried out with at least one of an undyed and undried cell.

7. The method of claim 1, wherein the method is carried out using a whole blood sample.

8. The method of claim 1, wherein a cell functionality is determined.

9. The method of claim 1, wherein a cell stage of the cell is determined.

10. The method claim 8, wherein the determining of the cell functionality includes determining an activation state of a cell and the detection of the height profile of the cell includes detecting a pathogen-affected cell.

11. The method of claim 9, wherein the determining of a cell stage of the cell includes differentiating a cell age.

12. The method of claim 1, wherein a physiological or morphological state of the cell is determined.

13. The method of claim 1, wherein an activity state of the cell is determined.

* * * * *